(12) United States Patent
Albertson-Kane et al.

(10) Patent No.: US 7,125,981 B2
(45) Date of Patent: Oct. 24, 2006

(54) NUCLEIC ACID FRAGMENTS FOR THE IDENTIFICATION OF BACTERIA IN INDUSTRIAL WASTEWATER BIOREACTORS

(75) Inventors: Helene M. Albertson-Kane, Thorofare, NJ (US); Michael G. Bramucci, Folsom, PA (US); Mario W. Chen, Chadds Ford, PA (US); Vasantha Nagarajan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 458 days.

(21) Appl. No.: 10/464,724

(22) Filed: Jun. 17, 2003

(65) Prior Publication Data
US 2003/0203398 A1  Oct. 30, 2003

Related U.S. Application Data

(62) Division of application No. 09/735,567, filed on Dec. 13, 2000, now Pat. No. 6,608,190.

(60) Provisional application No. 60/171,140, filed on Dec. 16, 1999.

(51) Int. Cl.
*C07H 21/04* (2006.01)
*C12Q 1/02* (2006.01)
*C12Q 1/04* (2006.01)
*C12Q 1/68* (2006.01)

(52) U.S. Cl. .................. 536/24.32; 435/29; 435/34; 435/6; 536/24.3; 536/24.1; 536/23.1

(58) Field of Classification Search ............. 435/29, 435/34, 6; 536/24.32, 24.1, 24.3, 23.1
See application file for complete search history.

(56) References Cited

FOREIGN PATENT DOCUMENTS

FR     2733754 A1 * 11/1996

OTHER PUBLICATIONS

Dojka et al., GenBank accession No. AF050574, Mar. 1998.*
Brauman et al., GenBank accession No. AY100737, 2003.*
Halos et al., GenBank accession No. DQ065813, 2005.*
Fournier et al., GenBank accession No. AF034809, 1999.*
Assinder and Williams, The TOL Plasmids: Determinants of the Catabolism of Toluene and the Xylenes, Adv. Microb. Physiol. 31:2-69(1990).
Williams and Sayers, The evolution of pathways for aromatic hydrocarbon oxidation in Pseudomonas, Biodegradation 5:195-217(1994).
Busse, H. et al., 1996, Classification and identification of bacteria: current approaches to an old problem. Overview of methods used in bacterial systematics. J. Biotechnol. 47(1):3-38.
Muyzer et al., 1996 Molecular methods to study the organization of microbial communities Water Sci. Technol., 32:1-9.
Ward, D.M., M. M. Bateson, R. Weller and A. L. Ruff-Roberts, 1992, Ribosomal RNA analysis of Microorganisms as they occur in nature. Adv. Microbial Ecol. 12:219-286. Woese, C. R. 1987.
Woese, C.R., Bacterial Evolution, Microbiol. Rev. 51-221-271, 1987.
Wagner, M., Amann, R., Lemmer, H., Schleifer, K. H. 1993. Probing activated sludge with oligonucleotides specific for proteobacteria; Appl. Environ. Microbiol. 59:1520-1525.
Genbank Accession No. U58015, Paracoccus sp. KS1, Jun. 20, 1998.
Genbank Accession No. D14320, *Brachymonas denitrificans*, Nov. 21, 1995.
Stackebrandt. E., and B. M. Goebel 1994. A place for DNA—DNA reassociation and 16S ribosomal-RNA sequence analysis in the present species definition in bacteriology. Int. J. Syst Bacteriol. 44; (4) 846-849.
Genbank, Accession No. U51101, denitrifying Fe<11>-oxidizing bacteria strain=BrGl, Mar. 30, 1997.
Genbank Accession No. X77450, Corynebacterium aquaticum, Jul. 19, 1994.
Genbank Accession No. AB02135, unidentified bacterium, Jul. 24, 2003.
Genbank Accession No. Y16927, *Paracoccus dentrificans*, May 7, 1999.
Genbank Accession.No. AB021349, unidentified bacterium, Jul. 24, 1999.
Genbank Accession No. AB021355, unidentified bacterium, Jul. 24, 2003.
Stackebrandt. Taxonomic Note: A Place for DNA—DNA Reassociation and 16S rRNA Sequence Analysis in the Present Species Definition in Bacteriology, Encyclopedia of Life Sciences, pp. 1-7, 2001.
Watanabe et al., Applied and Environmental Microbiology, 65(7), pp. 2813-2819, 1999.
Watanabe et al., GenEMBL accession No. AB021349, Jul. 1999.

* cited by examiner

*Primary Examiner*—Delia M. Ramirez

(57) ABSTRACT

Unique bacterial strains and identifying 16S rDNA sequences have been isolated from activated wastewater sludge. The 16S rDNA sequences are diagnostic for organisms which are key to the health of activated sludge wastewater systems.

2 Claims, No Drawings

NUCLEIC ACID FRAGMENTS FOR THE IDENTIFICATION OF BACTERIA IN INDUSTRIAL WASTEWATER BIOREACTORS

This application claims the benefit of U.S. patent application Ser. No. 09/735,567, filed Dec. 13, 2000 now U.S. Pat. No. 6,608,190, which claims the benefit of Provisional Application 60/171,140, filed Dec. 16, 1999.

FIELD OF THE INVENTION

This invention relates to the field of molecular biology and microbiology. More specifically, 16S rRNA regions have been identified and isolated from several previously unrecognized bacteria from an industrial wastewater bioreactor. Probes and primers corresponding to the unique regions have been constructed to enable the rapid identification of these bacteria in wastewater bioreactors. The metabolic characteristics of the newly defined species have been proposed.

BACKGROUND

Wastewater biotreatment is a cost effective, environmentally benign technology that is widely used by municipalities and industry to treat municipal waste or process waste. A variety of different processes that use microbes to remove inorganic and organic chemicals from industrial wastewater are known to those skilled in the art. For example, the activated sludge process is one common method. An activated sludge system usually involves a continuous flow process in which wastewater is mixed with sludge and aerated (Bitton, G. 1994. *Wastewater Microbiology*. Wiley-Liss, New York). The key feature of an activated sludge system is that some sludge is recycled from a settling tank back into the main reactor. The sludge is composed of bacteria and other microorganisms that utilize organic and inorganic chemicals in the wastewater as sources of nutrients and energy for growth. By utilizing the chemicals in the wastewater for metabolism and growth, the microorganisms incorporate the chemicals into new microorganisms and/or convert the chemicals into gases such as carbon dioxide and nitrogen, thereby removing the chemicals from the wastewater. Activation of sludge through recycling maintains a large population of microbes in the main reactor vessel to degrade the waste chemicals.

In general, a large variety of different types of bacteria may be found in a wastewater bioreactor. Bacteria belonging to the following genera are some of the bacteria that are likely to be present in a wastewater bioreactor: *Acinetobacter, Bacillus, Brevibacterium, Comomonas, Flavobacterium, Pseudomonas,* and *Zooglea* (Bitton, G. 1994. supra). The performance of a wastewater bioreactor is determined in part by the types of bacteria in the bioreactor because each bacterium growing in the bioreactor must have the right genes encoding biochemical pathways to use at least some of the different organic and inorganic chemicals available in the wastewater for energy and nutrients.

One example of a biochemical pathway that allows bacteria to use organic chemicals that might be in wastewater involves aromatic compounds such as toluene which are commonly found in industrial wastewater. The well characterized TOL plasmid pWWO contains xyl genes that encode enzymes for metabolism of toluene. These genes are organized into two operons (Assinder and Williams, *Adv. Microb. Physiol.* 31:2–69 (1990)). The upper pathway operon encodes the enzymes for oxidation of toluene to benzoate. The lower pathway operon encodes the 1,2-dioxygenase and benzoate dihydrodiol dehydrogenase that convert benzoate into catechol, the 2,3-catechol oxygenase that opens the aromatic ring of catechol, and the enzymes that then oxidize the resulting 2-hydroxy-muconic semialdehyde to intermediates of the TCA cycle. The TOL pathway typifies the general strategy that is used by many different bacteria to degrade a large variety of other aromatic compounds (Williams and Sayers, *Biodegradation* 5:195–217 (1994)), i.e., the aromatic compound is first converted to catechol or a substituted catechol, the aromatic ring of the catechol is opened in the second stage, and finally in the third stage of degradation, the ring cleavage product is converted to small aliphatic compounds that enter central metabolism. Hence, an influent containing aromatic compounds will favor growth of bacteria in the bioreactor that have the TOL pathway and/or funtionally similar pathways.

A bioreactor can be designed and operated to take advantage of different microbial activities. For example, the activated sludge process can be modified to encourage denitrification for removal of nitrate from wastewater (Bitton, G. 1994. supra). Dentrification is a process that involves anaerobic respiration during which nitrate serves as an electron acceptor in place of oxygen. During the course of denitrification, nitrate is reduced stepwise to elemental nitrogen ($NO_3 \rightarrow NO_2 \rightarrow NO \rightarrow N_2O \rightarrow N_2$) which is released to the atmosphere because of low water solubility. Optimum denitrification requires anoxic conditions because $O_2$ represses denitrification. The most widespread genra containing denitrifying bacteria are probably *Pseudomonas* and *Alcaligenes* but other genera containing denitrifiers are common (Bitton, G. 1994. supra).

It is evident from the foregoing discussion that successful wastewater biotreatment with an activated sludge process and other biological processes requires that the appropriate microbes be present in the bioreactor. Optimum performance of the bioreactor involves monitoring and adjusting physical parameters such as pH and dissolved oxygen to maintain an appropriate environment for microbial metabolism. Failure of a wastewater bioreactor, as indicated by unacceptably high levels of chemicals in the effluent water, could result from a variety of problems, including loss of necessary microorganisms from the biotreatment system. Accordingly, routine monitoring of the types of microorganisms in a wastewater bioreactor would be useful in evaluating bioreactor performance and for anticipating system failures.

Rapid and accurate identification is essential for routine monitoring of wastewater bioreactor microorganisms. Traditional methods of microbial identification involve culturing the organism to be identified and performing standard tests that reveal biochemical characteristics of the organism (Busse, H., J., Denner, E. B., Lubitz W. 1996. Classification and identification of bacteria: current approaches to an old problem. Overview of methods used in bacterial systematics. *J. Biotechnol.* 47(1):3–38). The results of the tests are used to search a database for an organism with the same characteristics. Such systems are not practical for routine monitoring of a wastewater bioreactor because of the large number of different isolates that would have to be cultured and tested daily.

Methods of microorganism identification that involve the use of DNA probes based on the sequences of ribosomal RNA (rRNA) molecules can be used to routinely test a sample for many different organisms rapidly and accurately (Busse, H., J., et al., supra); Muyzer, G., and N. B. Ramsing.

1996. Molecular methods to study the organization of microbial communities. *Water Sci. Technol.* 32:1–9). All cells contain ribosomes. Each ribosome is composed of three distinct rRNA molecules and a variety of protein molecules. In bacteria, the medium sized rRNA molecule, i.e., the 16S rRNA molecule, is particularly useful for identifying bacteria (Ward, D. M., M. M. Bateson, R. Weller, and A. L. Ruff-Roberts 1992. Ribosomal RNA analysis of Microorganisms as they occur in nature. *Adv. Microbial Ecol.* 12:219–286; Woese, C. R. 1987. Bacterial Evolution. *Microbiol. Rev.* 51:221–271). The nucleotide sequence of the 16S rRNA molecule has conserved regions that are present in most if not all bacteria and variable regions that can be used to distinguish species and subspecies. Since a rRNA molecule is a direct gene product that results from transcription of a corresponding rRNA gene (rDNA), rDNA can be specifically and rapidly isolated from a particular microorganism or a mixture of microorganisms by using appropriate DNA primers and the polymerase chain reaction (PCR) to amplify the rDNA. The pattern of fragments resulting from cutting the PCR product with a set of restriction endonucleases can be used to identify the organism from which the rDNA was amplified (Busse, H. J., et al., supra). Alternatively, in situ hybridization techniques are known whereby fluorescent probes based on specific 16S rRNA sequences can be used to demonstrate the presence of specific bacteria in samples of sludge (Wagner, M., Amann, R., Lemmer, H., Schleifer, K. H. 1993. Probing activated sludge with oligonucleotides specific for proteobacteria: inadequacy of culture-dependent methods for describing microbial community structure. *Appl. Environ. Microbiol.* 59:1520–1525).

The problem to be overcome is to rapidly identify microorganisms that may be found in a wastewater bioreactor so that the presence or absence of those microorganisms in the wastewater bioreactor can be monitored. The Applicants have solved the stated problem by identifying some of the bacteria that are present in a wastewater bioreactor and by providing sets of nucleic acid sequences that are unique to various novel bacterial strains that were isolated from an industrial wastewater bioreactor. The present invention has utility in that the provided sets of nucleic acid sequences can be used to identify and monitor the corresponding bacterial strains in samples taken from a wastewater bioreactor or from any environment which might contain the specified bacteria.

BRIEF DESCRIPTION OF THE SEQUENCE LISTING

Applicant(s) have provided 30 sequences in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Adminstrative Instructions). The symbols and format used for nucleotide and amino acid sequence data comply with the rules set forth in 37 C.F.R. §1.822.

SEQ ID NO:1 is the nucleotide sequence of the 16S rDNA corresponding to strain EMB14A.

SEQ ID NO:2 is the nucleotide sequence of the 16S rDNA corresponding to strain NBYE13.

SEQ ID NO:3 is the nucleotide sequence of the 16S rDNA corresponding to strain RA1.

SEQ ID NO:4 is the nucleotide sequence of the 16S rDNA corresponding to strain RA2.

SEQ ID NO:5 is the nucleotide sequence of the 16S rDNA corresponding to strain RA3.

SEQ ID NO:6 is the nucleotide sequence of the 16S rDNA corresponding to strain RA6.

SEQ ID NO:7 is the nucleotide sequence of the 16S rDNA corresponding to strain RA9.

SEQ ID NOs:8–15 correspond to primers used in amplification of various 16S rDNA fragments.

SEQ ID NOs:16–17 correspond to regions on the 16S rDNA which are diagnostic for the strain EMB14a.

SEQ ID NO:18 corresponds to regions on the 16S rDNA which is diagnostic for the strain NBYE13.

SEQ ID NOs:19–22 correspond to regions on the 16S rDNA which are diagnostic for the strain RA1.

SEQ ID NOs:23–24 correspond to regions on the 16S rDNA which are diagnostic for the strain RA2.

SEQ ID NOs:25–26 correspond to regions on the 16S rDNA which are diagnostic for the strain RA6.

SEQ ID NOs:27–28 correspond to regions on the 16S rDNA which are diagnostic for the strain RA9.

SEQ ID NOs:29–30 correspond to regions on the 16S rDNA which are diagnostic for the strain RA3.

SUMMARY OF THE INVENTION

The present invention provides an isolated 16S rDNA sequence indicative of the presence of an activated sludge bacterial strain selected from the group consisting of: (a) SEQ ID NO:1, SEQ ID NO:2, SEQ ID NO:3, SEQ ID NO:4, SEQ ID NO:5, SEQ ID NO:6 and SEQ ID NO:7; (b) an isolated nucleic acid molecule that hybridizes with (a) under the following hybridization conditions: 6×SSC (1 M NaCl), 50% formamide, 1% SDS at 37° C., and a wash in 0.1×SSC at 60 to 65° C.; (c) an isolated nucleic acid molecule that has at least 97% identity to (a); and (d) an isolated nucleic acid molecule that is completely complementary to (a), (b) or (c).

Additionally the invention provides an isolated 16S rDNA sequence indicative of an activated sludge bacterial strain from the group consisting of: (a) SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:30; (b) an isolated nucleic acid molecule that hybridizes with (a) under the following hybridization conditions: 6×SSC (1 M NaCl), 50% formamide, 1% SDS at 37° C., and a wash in 0.1×SSC at 60 to 65° C.; (c) an isolated nucleic acid molecule that has at least 97% identity to (a); and (d) an isolated nucleic acid molecule that is completely complementary to (a), (b) or (c).

Similarly the invention provides a method for identifying an activated sludge bacterial strain comprising:
  (i) extracting genomic DNA from a cell isolated from activated sludge; and
  (ii) amplifying the extracted genomic DNA with at least one oligonucleotide primer corresponding to a portion of any one of the 16S rDNA sequences of the present invention such that amplification products are generated; wherein the presence of amplification products confirms the presence of activated sludge bacterial strain.

Additionally the invention provides isolated bacterial strains capable of degrading pyruvate, acetate, benzoate and of reducing nitrate.

In a preferred embodiment the invention provides methods for the degradation of a pyruvate, acetate or benzoate comprising contacting the bacterial strain of the invention under suitable growth conditions with an effective amount of substrate whereby the substrate is degraded.

Similarly the invention provides a method for the reduction of nitrate comprising contacting the bacterial strain of the present invention under suitable growth conditions with an effective amount of nitrate whereby the nitrate is reduced.

DETAILED DESCRIPTION OF THE INVENTION

The present invention provides unique 16S rDNA sequence profiles derived from activated sludge bacteria. All relevant activated sludge bacterial stains were isolated from an industrial wastewater bioreactor. The instant sequence profiles may be used to identify and sub-type bacteria key in the activated sludge process. Each 16S rDNA profile is unique having less than 97% identity to known sequences. In addition to the full 16S rDNA sequences, specific regions of the 16S rDNA profiles have been identified as being diagnostic for bacteria that are capable of pyruvate, acetate, benzoate degradation as well as denitrification reactions.

In this disclosure, a number of terms and abbreviations are used. The following definitions are provided.

The terms "EMB14A, NBYE13, RA1, RA2, RA3, RA6, and RA9" will refer to activated sludge bacterial strains of the instant invention containing the instant 16S rDNA profiles.

The term "activated sludge bacteria or bacterium" or "activate sludge bacterial strains" refers bacteria contained in activated sludge. Typically these organisms are drawn from genera including but not limited to *Acinetobacter, Bacillus, Brevibacterium, Comomonas, Flavobacterium, Pseudomonas,* and *Zooglea*. Within the general class of activated sludge bacteria are a number of species that will have the ability to degrade and metabolize a variety of organic substrates. Within the context of the present invention, bacteria that degrade and metabolize pyruvate, acetate, and benzoate have been isolated and identified and will be referred to as "pyruvate" or "acetate" or "benzoate" "degrading bacteria" or "strains" respectively. Similarly activated sludge bacteria will also comprise species that have the ability to reduce nitrate or nitrite to inorganic nitrogen. Such strains will be referred to herein as "denitrifying bacterial strains" or "denitrifying bacteria" and will apply a bacteria that has the ability to reduce nitrate to inorganic nitrogen according to the following scheme:

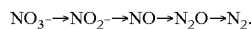

$NO_3^- \rightarrow NO_2^- \rightarrow NO \rightarrow N_2O \rightarrow N_2$.

The term "activated sludge" will mean the bacteria and other microorganisms in a wastewater bioreactor that are generated during wastewater treatment and utilize organic and inorganic chemicals in the wastewater as sources of nutrients and energy for growth, thereby removing the chemicals from the wastewater.

The term "16S rDNA" will refer to the DNA encoding 16S ribosomal RNA found within bacterial cells.

The term "16S rDNA profile" will refer to the specific DNA sequence of the rDNA gene in any particular organism. For the purposes of the present invention the 16S rDNA profiles for EMB14A, NBYE13,RA1,RA2,RA3,RA6, and RA9 are shown in SEQ ID NOs:1–7.

The term "diagnostic" as applied to the use of 16S rDNA sequences or to regions of high base homology to those sequences means a sequence which may be used either as a hybridization probe under stringent conditions or a PCR primer that will correctly identify the 16S rDNA sequence in question. As used herein SEQ ID NOs:16–17are diagnostic for 16S rDNA isolated from strain EMB114a; SEQ ID NO:18 is diagnostic for 16S rDNA isolated from strain NBYE13; SEQ ID NOs:19–22 are diagnostic for 16S rDNA isolated from strain RA1; SEQ ID NOs:23–24 are diagnostic for 16S rDNA isolated from strain RA2; SEQ ID NOs:29–30 are diagnostic for 16S rDNA isolated from strain RA3; SEQ ID NOs:25–26 are diagnostic for 16S rDNA isolated from strain RA6; and SEQ ID NOs:27–28 are diagnostic for 16S rDNA isolated from strain RA9.

The letters "A", "G", "T", "C" when referred to in the context of nucleic acids will mean the purine bases Adenine (C5H5N5), Guanine (C5H5N5O) and the pyrimidine bases Thymine (C5H6N2O2) and Cytosine (C4H5N3O) respectively.

"Gene" refers to a nucleic acid fragment that expresses a specific protein, including regulatory sequences preceding (5' non-coding sequences) and following (3' non-coding sequences) the coding sequence.

The term "isolated nucleic acid fragment" will refer to a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

The term "oligonucleotide" refers to primers, probes, oligomer fragments to be detected, labeled-replication blocking probes, oligomer controls, and shall be generic to polydeoxyribonucleotides (containing 2-deoxy-D-ribose), to polyribonucleotides (containing D-ribose) and to any polynucleotide which is an N glycoside of a purine or pyrimidine base (nucleotide), or modified purine or pyrimidine base. Also included in the definition of "oligonucleotide" are nucleic acid analogs (e.g., peptide nucleic acids) and those that have been structurally modified (e.g., phosphorothioate linkages). There is no intended distinction between the length of a "nucleic acid", "polynucleotide" or an "oligonucleotide".

The term "primer" refers to an oligonucleotide (synthetic or occurring naturally), which is capable of acting as a point of initiation of nucleic acid synthesis or replication along a complementary strand when placed under conditions in which synthesis of a complementary stand is catalyzed by a polymerase. Typically, short oligonucleotides of 12–15 bases may be used as amplification primers in PCR in order to obtain a particular nucleic acid fragment comprising the primers.

The term "probe" refers to an oligonucleotide (synthetic or occurring naturally), that is significantly complementary to a "fragment" and forms a duplexed structure by hybridization with at least one strand of the fragment. Typically, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques).

The term "complementary" is used to describe the relationship between nucleotide bases that are hybridizable to one another. For example, with respect to DNA, adenosine is complementary to thymine and cytosine is complementary to guanine.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 6×SSC (1 M NaCl), 30 to 35% formamide, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 6×SSC (1 M NaCl), 40 to 45% formamide, 1% SDS at 37° C., and a wash in 0.5× to 1×SSC at 55 to 60° C. Exemplary high stringency conditions include hybridization in 6×SSC (1 M NaCl), 50% formamide, 1% SDS at 37° C., and a wash in 0.1×SSC at 60 to 65° C.

Specificity is typically the function of post-hybridization washes, the critical factors being the ionic strength and temperature of the final wash solution. The melting temperature ($T_m$) of a probe-target hybrid can be calculated to provide a starting point for the determination of correct stringency conditions. For DNA—DNA hybrids, the $T_m$ can be approximated from the equation of Meinkoth and Wahl, *Anal Biochem.*, 138:267–284 (1984): $T_m$=81.5° C.+16.6 (log M)+0.41(% G+C)−0.61 (% form)−500/L, where M is the molarity of monovalent cations, % G+C is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. Thus, for example, sequences that will hybridize to the 16S rDNA nucleic acid sequence of strain EMB14a (SEQ ID NO:1) under stringent conditions will include but are not limited to those sequences set forth in SEQ ID NOs:16–17. Those sequences that will hybridize to the 16S rDNA nucleic acid sequence of strain NBYE13 (SEQ ID NO:2) under stringent conditions will include but are not limited to the sequence set forth in SEQ ID NO:18. Those sequences that will hybridize to the 16S rDNA nucleic acid sequence of strain RA1 (SEQ ID NO:3) under stringent conditions will include but are not limited to those sequences set forth in SEQ ID NOs:19–22. Similarly, those sequences that will hybridize to the 16S rDNA nucleic acid sequence of strain RA2 (SEQ ID NO:4) under stringent conditions will include but are not limited to those sequences set forth in SEQ ID NOs:23–24. Likewise, those sequences that will hybridize to the 16S rDNA nucleic acid sequence of strain RA3 (SEQ ID NO:5) under stringent conditions will include but are not limited to those sequences set forth in SEQ ID NOs:29–30. Additionally, those sequences that will hybridize to the 16S rDNA nucleic acid sequence of strain RA6 (SEQ ID NO:6) under stringent conditions will include but are not limited to those sequences set forth in SEQ ID NOs:25–26. Similarly, those sequences that will hybridize to the 16S rDNA nucleic acid sequence of strain RA9 (SEQ ID NO:7) under stringent conditions will include but are not limited to those sequences set forth in SEQ ID NOs:27–28.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995).

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Preferred computer program methods to determine identity and similarity between two sequences include, but are not limited to, the GCG Pileup program found in the GCG program package, as used in the instant invention, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, and FASTA (Pearson et al., *Proc. Natl. Acad. Sci. U.S.A.* 85:2444–2448 (1988). The BLAST X program is publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J. Mol.*

*Biol.* 215:403–410 (1990)). Another preferred method to determine percent identity, is by the method of DNASTAR protein alignment protocol using the Jotun-Hein algorithm (Hein et al., *Methods Enzymol.* 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

The term "amplification product" refers to portions of nucleic acid fragments that are produced during a primer directed amplification reaction. Typical methods of primer directed amplification include polymerase chain reaction (PCR), ligase chain reaction (LCR) or Strand displacement Amplification (SDA). If PCR methodology is selected, the replication composition would include for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions would comprise, for example, a thermostable ligase, e.g., *T. aquaticus* ligase, two sets of adjacent oligonucleotides wherein one member of each set is complementary to each of the target strands, Tris HCl buffer, KCl, EDTA, NAD, dithiothreitol and salmon sperm DNA. See, for example, Tabor et al., *Proc. Acad. Sci. U.S.A.,* 82, 1074–1078 (1985)).

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc., 1282 S. Park St. Madison, Wis. 53715 USA). Within the context of this application it will be understood that where sequence analysis software is used for analysis, that the results of the analysis will be based on the "default values" of the program referenced, unless otherwise specified. As used herein "default vales" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*,Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention provides a variety of strains isolated from a wastewater bioreactor that have been characterized on the basis of 16S rDNA sequences as well as metabolic behavior. The strains have the ability to degrade various compounds including acetate, pyruvate, benzoate and nitrate. Additionally the invention provides the 16S rDNA sequences of each of these organisms as well as various regions of those sequences that are particularly diagnostic for the strain from which it was isolated.

Isolation and Characterization of Bacterial Strains

The bacterial community structure of activated sludge of a wastewater can be investigated by use of the rRNA approach. A combination of direct retrieval of rRNA sequences and whole-cell oligonucleotide probing can then be used to detect specific rRNA sequences of uncultured bacteria in natural samples and to microscopically identify individual cells. All bacteria contain ribosomes composed of three distinct rRNA molecules. The 16S rRNA molecule is particularly useful for identifying bacteria because there are more 16S rRNA sequences than 5S or 23S rRNA sequences available in nucleotide databases (Ludwig, W. and K. Schleifer. 1999. Phylogeny of Bacteria beyond the 16S rRNA standard. ASM News 65:752–757). The nucleotide sequence of the 16S rRNA molecule has conserved regions that are present in most if not all bacteria and variable regions that can be used to distinguish species and subspecies (Ward, D. M., M. M. Bateson, R. Weller, and A. L. Ruff-Roberts. 1992. Ribosomal RNA analysis of Microorganisms as they occur in nature. *Adv. Microbial Ecol.* 12:219–286; Woese, C. R. 1987. Bacterial Evolution. *Microbiol. Rev.* 51:221–271). Since a rRNA molecule is a direct gene product that results from transcription of a corresponding rRNA gene (rDNA), 16S rRNA sequences can be obtained by specifically and rapidly amplifying the 16S rDNA from a particular microorganism or a mixture of microorganisms by using appropriate DNA primers and the polymerase chain reaction (PCR). DNA primers directed against highly conserved regions of the 16S rDNA that are present in all known bacteria can be used to amplify 16S rDNA by PCR from any bacterial cell. The highly conserved regions that are used to amplify the 16S rDNA flank variable and highly variable regions that differ from one bacterial species to another. Therefore, sequencing amplified 16S rDNA from a new bacterial isolate enables one skilled in the art to use the new 16S rDNA sequence as the query sequence in a BLAST search of the GenBank nucleotide sequence database and determine if the 16S rDNA of the new bacterial isolate is similar to any 16S rDNA that has been previously isolated, sequenced, and deposited in GenBank. If the query 16S rDNA sequence is less than 97% identical to any 16S rDNA sequence previously known in the art, then the query sequence has probably been derived from a previously unrecognized bacterial species (Stackebrandt, E., and B. M. Goebel. 1994. A place for DNA—DNA reassociation and 16S ribosomal-RNA sequence analysis in the present species definition in bacteriology. *Int. J. Syst. Bacteriol.* 44: (4) 846–849).

Within the context of the present invention seven new strains of activated sludge bacteria have been identified on the basis of 16S rDNA sequences. Comparison of the present sequences with public databases revealed that none had any greater identity with known sequences than 95%. Accordingly, it is within the scope of the present invention to provide 16S rDNA sequences that are at least 95% identical to the present sequences, where sequences that are at least 97% identical are preferred and where sequences that are at least 99% identical are most preferred.

DNA probes and primers can be designed for detection of particular bacterial species in complex mixtures of microorganisms (Amann, R. I., W. Ludwig, and K. Schleifer. 1995. Phylogenetic identification and in situ detection of individual microbial cells without cultivation. *Microbiol Rev.* 59:143–169). The principal steps in designing appropriate probes to detect a specific microorganism include alignment of 16S rDNA sequences and identification of sequence idiosyncrasies, i.e., identification of the specific variable and highly variable regions in a 16S rDNA sequence. Successful wastewater treatment with an activated sludge process and other biological processes requires that the appropriate microbes be present in the treatment system. Hence, the presence of variable and highly variable regions in 16S rDNA sequences enables one skilled in the art to design DNA probes to determine if the necessary bacteria are present in a wastewater bioreactor or other process that involves a complex mixture of microorganisms (Wagner, M., Amann, R., Lemmer, H., Schleifer, K. H. 1993. Probing activated sludge with oligonucleotides specific for proteobacteria: inadequacy of culture-dependent methods for describing microbial community structure. *Appl. Environ. Microbiol.* 59: 1520–1525).

Probes and primers useful in the present invention are those that are diagnostic for a particular 16S rDNA sequence. Particularly useful probes and primers include, but are not limited to those set forth in SEQ ID NOs:16–17 which are diagnostic for 16S rDNA isolated from strain EMB114a; SEQ ID NO:18 which is diagnostic for 16S rDNA isolated from strain NBYE13; SEQ ID NOs:19–22 which are diagnostic for 16S rDNA isolated from strain RA1; SEQ ID NOs:23–24 which are diagnostic for 16S rDNA isolated from strain RA2; SEQ ID NOs:29–30 which are diagnostic for 16S rDNA isolated from strain RA3; SEQ ID NOs:25–26 which are diagnostic for 16S rDNA isolated from strain RA6; and SEQ ID NOs:27–28 which are diagnostic for 16S rDNA isolated from strain RA9.

Metabolic Analysis of Strains

Bacteria utilize organic and inorganic compounds in wastewater as sources of nutrients and energy for growth. Utilization of the organic and inorganic compounds in wastewater for growth means that bacteria must chemically alter the molecular structure of the organic and inorganic compounds in wastewater. One reason that bacteria must chemically alter the wastewater compounds is that the compounds do not necessarily have molecular structures that can be incorporated directly into cellular structures. A second reason is that the wastewater compounds do not necessarily have molecular structures that allow the energy contained in the chemical bonds of the wastewater compounds to be directly used by bacteria for cellular activities that require energy. Activated sludge bacteria use various biochemical pathways to chemically convert the wastewater compounds into other compounds that can be directly incorporated into cellular structures or used to directly provide energy for cellular activities. In general, chemical alteration of wastewater compounds by bacteria involves breaking chemical bonds in the molecules of the wastewater compounds. Breaking the chemical bonds in the wastewater compounds results in converting a single molecule into two or more smaller molecules. Hence, the bacteria are typically described as "degrading" the wastewater compounds. By utilizing the compounds in wastewater for metabolism and growth, the microorganisms incorporate the chemicals into cellular structures and new microorganisms. Wastewater compounds are chemically modified to obtain energy in reactions such as chemical oxidation of carbon compounds to form carbon dioxide or chemical reduction of nitrate to form nitrogen. Conversion of the wastewater compounds to cellular structures or gases results in removal of the chemicals from the wastewater.

Degradation of organic compounds such as benzoate and catechol provide activated sludge bacteria with small carbon compounds that can be used to synthesize cellular structures and with energy for cellular activites. The well characterized TOL plasmid pWWO contains xyl genes that encode enzymes for metabolism of benzoate and catechol (Assinder and Williams, *Adv. Microb. Physiol.* 31:2–69 (1990)). Plasmid pWWO encodes a 1,2-dioxygenase and benzoate dihydrodiol dehydrogenase that convert benzoate into catechol, the 2,3-catechol oxygenase that opens the aromatic ring of catechol, and several enzymes that then oxidize the resulting 2-hydroxymuconic semialdehyde to pyruvic acid and acetaldehyde. The pyruvic acid and acetaldehyde can be used for synthesis of cellular components or further oxidized through the TCA cycle to provide energy.

In addition to organic molecules, inorganic molecules can be degraded. Denitrification is a process that involves anaerobic respiration during which nitrate serves as an electron acceptor in place of oxygen (Bitton, G. 1994. supra). During the course of denitrification, nitrate is chemically reduced stepwise to elemental nitrogen ($NO_3 \rightarrow NO_2 \rightarrow NO \rightarrow N_2O \rightarrow N_2$) which is released to the atmosphere because of low water solubility. Denitrification is catalyzed by a series of enzymes found in certain bacteria such as those belonging to the genera *Pseudomonas, Bacillus, Acinetobacter,* and others. The enzymes include nitrate reductase, nitrite reductase, nitric oxide reductase, and nitrous oxide reductase.

Accordingly, the present invention provides isolated activated sludge bacterial strains which possess the ability to degrade and metabolize a variety of organics, including, but not limited to pyruvate, acetate, benzoate and nitrate. The present strains and their identifying characteristic are summarized below in Table 1.

TABLE 1

| Strain | 16S rDNA | Diagnostic Sequence | Significant base Identity | Putative Species | Metabolic Substrates |
| --- | --- | --- | --- | --- | --- |
| EMB14a | SEQ ID NO:1 | SEQ ID NO:16–17 | 95% with U58015* | Paracoccus sp | Pyruvate Nitrate |
| NBYE13 | SEQ ID NO:2 | SEQ ID NO:18 | 92% with D14320* | Brachymonas | Pyruvate Beuzoate |

TABLE 1-continued

| Strain | 16S rDNA | Diagnostic Sequence | Significant base Identity | Putative Species | Metabolic Substrates |
|---|---|---|---|---|---|
| RA1 | SEQ ID NO:3 | SEQ ID NO:19–22 | 94% with U51101* | Denitrifying bacteria | Acetate |
| RA2 | SEQ ID NO:4 | SEQ ID NO:23–24 | 95% with U51101* | Denitrifying bacteria | Acetate |
| RA3 | SEQ ID NO:5 | SEQ ID NO:29–30 | 95% with X77450* | Corynebacterium Microbacterium | Pyruvate |
| RA6 | SEQ ID NO:6 | SEQ ID NO:25–26 | 92% with D14320* | Brachyrnonas | Pyruvate Benzoate Nitrate |
| RA9 | SEQ ID NO:7 | SEQ ID NO:27–28 | 92% with D14320* | Brachymonas | Pyruvate Benzoate |

*Genbank Accession Number

Assay Methods:

The instant sequences may be used in a variety of formats for the detection of activated sludge bacteria. The two most convenient formats will rely on methods of nucleic acid hybridization or primer directed amplification methods such as PCR.

Nucleic Acid Hybridization Methods:

The basic components of a nucleic acid hybridization test include a probe, a sample suspected of containing an activated sludge bacteria (for example bacteria that are instrumental in degradation of aromatic compounds and denitrifying reactions) and a specific hybridization method. As noted above, probes of the present invention are single strand nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base. A probe may be composed of either RNA or DNA. The form of the nucleic acid probe may be a marked single strand molecule of just one polarity or marked single strand molecule having both polarities present. The form of the probe, like its length, will be determined by the type of hybridization test to be done.

The sample may or may not contain the organism of interest. The sample may take a variety of forms, including liquid such as water, or solid such as dust, or soil. The sample nucleic acid must be made available to contact the probe before any hybridization of probe and target molecule can occur. Thus the organism's RNA must be free from the cell and placed under the proper conditions before hybridization can occur. Methods of in solution hybridization necessitate the purification of the RNA in order to be able to obtain hybridization of the sample rRNA with the probe. This has meant that to utilize the in solution method for detecting target sequences in a sample, the nucleic acids of the sample must first be purified to eliminate protein, lipids, and other cell components, and then contacted with the probe under hybridization conditions. Method for the purification of the sample nucleic acid are common and well known in the art (Maniatis, supra).

Similarly, hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed.

In one embodiment, hybridization assays may be conducted directly on bacterial lysates, without the need to extract the nucleic acids. This eliminates several steps from the sample-handling process and speeds up the assay. To perform such assays on crude cell lysates, a chaotropic agent is typically added to the cell lysates prepared as described above. The chaotropic agent stabilizes nucleic acids by inhibiting nuclease activity. Furthermore, the chaotropic agent allows sensitive and stringent hybridization of short oligonucleotide probes to RNA at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Alternatively, one can purify the rRNA prior to probe hybridization. A variety of methods are known to one of skill in the art (e.g., phenol-chloroform extraction, IsoQuick extraction (MicroProbe Corp., Bothell, Wash.), and others). Pre-hybridization purification is particularly useful for standard filter hybridization assays. Furthermore, purification facilitates measures to increase the assay sensitivity by incorporating in vitro RNA amplification methods such as self-sustained sequence replication (see for example Fahy et al. (1991) in *PCR Methods and Applications*, Cold Spring Harbor Laboratory Press, pp. 25–33) or reverse transcriptase PCR (Kawasaki (1990) in *PCR Protocols: A Guide to Methods and Applications*, M. A. Innis et al., eds., pp. 21–27). One can obtain amplified rRNA by using in vitro RNA amplification techniques as described in Fahy et al., supra.; Kawasaki, supra. The exact procedure used is not crucial, provided that it does not amplify significant amounts of DNA, which would tend to obscure results.

Once the pre-rRNA is released from the cells, it can be detected by any of a variety of methods. The method of rRNA detection is not crucial to the invention. However, the most useful embodiments have at least some of characteristics of speed, convenience, sensitivity, and specificity. Direct DNA probe analysis is suitable, as is an in vitro RNA amplification method, such as 3SR, that employs labelled primers.

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the rRNA sequence. Preferred are those probes that hybridize to regions of the rRNA that have minimal secondary and tertiary interactions. The advantage of such probes is that the hybridization can be carried out without the additional step of heat denaturing the sample nucleic acid. For example, the hybridization can be carried out at room temperature.

The sandwich assay may be encompassed in an assay kit. This kit would include a first component for the collection of samples from soil such as vials for containment, and buffers for the disbursement and lysis of the sample. A second component would include media in either dry or liquid form for the hybridization of target and probe polynucleotides, as well as for the removal of undesirable and nonduplexed forms by washing. A third component includes a solid support (dipstick) upon which is fixed or to which is conjugated unlabeled nucleic acid probe(s) that is (are) complementary to a part of the precursor rRNA of the species of bacteria being tested. In the case of multiple target analysis more than one capture probe, each specific for its own rRNA, will be applied to different discrete regions of the dipstick. A fourth component would contain labeled probe that is complementary to a second and different region of the same rRNA strand to which the immobilized, unlabeled nucleic acid probe of the third component is hybridized.

In another embodiment, the instant 16S rDNA sequence may be used as a 3' blocked detection probe in either a homogeneous or heterogeneous assay format. For example a probe generated from the instant sequences may be 3' blocked or non-participatory and will not be extended by, or participate in, a nucleic acid amplification reaction. Additionally, the probe incorporates a label that can serve as a reactive ligand that acts as a point of attachment for the immobilization of the probe/analyte hybrid or as a reporter to produce detectable signal. Accordingly, genomic or cDNA isolated from the test organism is amplified by standard primer-directed amplification protocols in the presence of an excess of the 16S rDNA 3' blocked detection probe to produce amplification products. Because the probe is 3' blocked, it does not participate or interfere with the amplification of the target. After the final amplification cycle, the detection probe anneals to the relevant portion of the amplified DNA and the annealed complex is then captured on a support through the reactive ligand.

PCR Assay Methods:

In embodiment the present sequences may be used as primers or to generate primers that may be used in primer directed nucleic acid amplification to detect the presence of activated sludge bacteria. A variety of primer directed nucleic acid amplification methods are known in the art including thermal cycling methods such as polymerase chain reaction (PCR) and ligase chain reaction (LCR) as well as isothermal methods and strand displacement amplification (SDA). The preferred method is PCR. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Hemdon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.).

If a nucleic acid target is to be exponentially amplified, then two primers are used each having regions complementary to only one of the stands in the target. After heat denaturation, the single-stranded target fragments bind to the respective primers which are present in excess. Both primers contain asymmetric restriction enzyme recognition sequences located 5' to the target binding sequences. Each primer-target complex cycles through nicking and polymerization/displacement steps in the presence of a restriction enzyme, a DNA polymerase and the three dNTP's and one dNTP[aS] as discussed above. An in depth discussion of SDA methodology is given by Walker et al., *Proc. Natl. Acad. Sci. U.S.A.*, 89, 392, (1992).

Alternatively, asymmetric amplification can be used to generate the strand complementary to the detection probe. Asymmetric PCR conditions for producing single-stranded DNA would include similar conditions for PCR as described however, the primer concentrations are changed with 50 pmol of the excess primer and 1 pmol of the limiting primer. It is contemplated that this procedure would increase the sensitivity of the method. This improvement in sensitivity would occur by increasing the number of available single strands for binding with the detection probe.

Within the context of the present invention, primers will be designed to variable regions of the 16S rDNA profile which will be diagnostic of particular bacteria.

Following amplification and prior to sequencing, the amplified nucleotide sequence may be ligated to a suitable vector followed by transformation of a suitable host organism with said vector. One thereby ensures a more readily available supply of the amplified sequence. Alternatively, following amplification, the amplified sequence or a portion thereof may be chemically synthesized for use as a nucleotide probe. In either situation the DNA sequence of the variable region is established using methods such as the dideoxy method (Sanger, F. et al. *Proc. Natl. Acad. Sci* (1977) 74, 5463–5467). The sequence obtained is used to guide the choice of the probe for the organism and the most appropriate sequence(s) is/are selected.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the FASTA algorithm (Pearson et at, *Proc. Natl. Acad. Sci. U.S.A.* 85:2444–2448 (1988)) and the BLAST family of programs which can be used for database similarity searches. The family includes BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995). Software for performing BLAST analyses is publicly available, e.g., through the National Center for Biotechnology Information and other sources (BLAST Manual, Altschul et al., Natl. Cent. Biotechnol. Inf., Natl. Library Med. (NCBI NLM) NIH, Bethesda, MD 20894; Altschul et al., *J. Mol. Biol.* 215:403–410 (1990)). Additionally the "CLUSTAL" algorithm was used (*Nucleic Acids Research*, 22:46734680) for sequence alignments.

Unless otherwise stated all sequence analysis algorithms employed default values.

The meaning of abbreviations is as follows: "h" means hour(s), "min" means minute(s), "sec" means second(s), "d" means day(s), "mL" means milliliters, "L" means liters.

Sludge:

A sample of aerobic activated sludge was obtained from a DuPont wastewater bioreactor. Glycerol was added to the sludge as a cryoprotectant (final concentration 15%). The sludge was aliquoted into 15 ml centrifuge tubes and stored at −70° C.

Culture Media and Isolation of Bacterial Strains:

Single colony cloning involved using methods well know to those skilled in the art to reinoculate a single colony onto the agar medium from which it was originally isolated by streaking the colony onto the surface of the agar medium so that the bacteria in the colony could again grow as individual colonies. This process was repeated several times until restreaking of a single colony of a particular type or morphology always gave rise to progeny colonies of the same type or morphology.

Amplification and Sequencing of 16S rDNA:

The 16S rDNA of each bacterial strain was amplified by PCR and sequenced as follows. A small loop full of cells was suspended in 200 µl of sterile water and heated for 10 minutes at 90° C. The cell lysate was then mixed again by vortexing for a few seconds, and 5 µl or 10 µof lysate was used as the template in a PCR reaction. PCR was performed in a Perkin Elmer GENEAMP™9600 with a commercial kit according to the manufacturer's instructions (PE Applied Biosystems, Perkin Elmer). Primers HK12(12 (GAG TTT GAT CCT GGC TCA G) [SEQ ID NO:8] and HK13 (TAC CTT GTT AGG ACT T) [SEQ ID NO:9] were used to amplify 16S rDNA. The PCR reactions were incubated at 95° C. for 5 minutes and then cycled 40 times at 94° C. for 30 seconds, 55° C. for 1 minute and 72° C. for 1 minute. The amplified DNA was purified using a commercial kit according to the manufacturer's instructions (QIAQUICK™PCR Purification Kit, Qiagen). The PCR products were sequenced on an automated ABI sequencer, using primers HK12, HK13, and HK14(GTG CCA GCA GYM GCG GT, where Y=C or T, M=A or C) [SEQ:10]. The 16S rDNA sequences were used as query sequences for a FastA searches (Wisconsin Package Version 9.0, Genetics Computer Group (GCG), Madison, Wis.) of GeneBank.

The rDNA of bacterial strains that had less than 96% sequence identity with any GenBank entry was again amplified and sequenced. Duplicate samples of the reamplified rDNA were sequenced using an extended set of primers that included HK12, HK13, HK14, HK27 (GTG CTC CCC CGC CAA TTC CT) [SEQ ID NO:11], HK28 (AGG AAT TGG CGG GGG AGC AC) [SEQ ID NO:12], HK36 (CAC GAG CTG ACG ACG ACA GCC AT) [SEQ ID NO:13], HK37 (ATG GCT GTC GTC AGC TCG TG) SEQ ID NO:14], and HK42 (ACC GCK RCT GCT GGC AC, where K=G or T, R=A or G) SEQ ID NO:15]. The new sequences were used as the query sequences for BLAST (NCBI) searches of GenBank.

Example 1

Isolation and Identification of Novel Bacteria from a Wastewater Bioreactor: Method 1

Example 1 demonstrates the isolation of several strains of bacteria from a wastewater bioreactor by using several types of standard microbiological agar media. The 16S rDNA sequences of these bacterial strains were no more than 95% identical to the 16S rDNA sequences of previously identified bacteria. The 16S rDNA sequences of these bacteria were significantly different from any 16S rDNA sequences known in the prior art.

A sample of sludge was thawed and serially diluted in sterile water. Aliquots of each dilution (0.2 ml) were spread onto several different types of standard microbiological agar media. The inoculated agar plates were incubated at 30° C. After 6 days, the agar plates were examined for growth. Several different types of bacterial colonies were present on most types of media. Representative colonies were identified for each medium. Each representative colony was used to establish a distinct bacterial strain by single colony cloning.

The initial FastA searches indicated that the rDNA sequences derived from EMB14A and NBYE13 had less than 96% identity with similar rDNA sequences in GenBank. Accordingly, the rDNA of these strains was again amplified and sequenced in duplicate using an extended primer set to verify their rDNA sequences. Using the verified sequences as the query sequences for BLAST searches of GenBank confirmed that both verified sequences had less than 96% identity with similar rDNA sequences in GenBank (Table 2).

16S rRNA sequences that have less than 97% identity are most likely derived from different bacterial species (Stackebrandt, E., and B. M. Goebel. 1994. A place for DNA-DNA reassociation and 16S ribosomal-RNA sequence analysis in the present species definition in bacteriology. *Int. J. Syst. Bacteriol.* 44: (4) 846–849). Since the 16S rDNA sequences derived from EMB14A and NBYE13 have less than 96% identical with the most similar 16S sequences already present in GenBank, the 16S rDNA sequences from EMB14A and NBYE13 are significantly different from any other 16S rDNA or 16S rRNA sequence previously known to the art.

TABLE 2

Comparison of 16S rDNA sequences from wastewater bacteria to GenBank sequences

| | | GenBank Sequence with Highest Identity | | |
|---|---|---|---|---|
| Strain | Isolation Medium | Accession No. | Type of Bacteria | % Identity |
| EMB14A | EMB | U58015 | *Paracoccus* sp. | 95 |
| NBYE13 | NYBE | D14320 | *Brachymonas denitrificans* | 92.0 |

Example 2

Isolation and Identification of Novel Bacteria from a Wastewater Bioreactor System: Method 2

Example 2 demonstrates the isolation of several strains of bacteria from a wastewater bioreactor by using an enrichment procedure. The 16S rDNA sequences of these bacterial strains were no more than 96% identical to the 16S rDNA sequences of previously identified bacteria. The 16S rDNA sequences of these bacteria were significantly different from any 16S rDNA sequences known in the prior art.

A sample of sludge was thawed. The particulate portion of the sludge was washed with 1× Tbase (2.0 g $(NH_4)_2SO_4$, 14.0 g $K_2HPO_4$, 6.0 g $KH_2PO_4$, 1.0 sodium citrate·$2H_2O$ in 1 liter water) by centrifuging the sludge at low speed, discarding the supernatent, and resuspending the pellet to the original sludge volume with 1× Tbase. A 2 ml aliquot of washed sludge was inoculated into a culture flask containing 18 ml of 1× Tbase. The culture was incubated in a shaking water bath at 25° C. After 20 hours of incubation, 1 ml of this culture was added to 9 ml of S15+1.0% glucose. The S15 culture was designated as WWS1 and incubated for 51 hours. Aliquots of WWS1 were frozen at −70° C.

An aliquot of WWS1 was thawed, diluted 1:$10^5$, and plated on R2A agar plates. The plates were incubated at 25° C. for 160 hours. Several different types of bacterial colonies were present on the R2A agar plates. Each representative colony was used to establish a distinct bacterial strain by single colony cloning.

The initial FastA searches indicated that the rDNA sequences derived from RA1, RA2, RA3, RA6, and RA9 had less than 96% identical with similar rDNA sequences in GenBank. Accordingly, the rDNA of these strains was again amplified and sequenced in duplicate using an extended primer set to verify their rDNA sequences. Using the verified sequences as the query sequences for BLAST searches of GenBank confirmed that all of the verified sequences had less than 96% identity with similar rDNA sequences in GenBank (Table 3).

16S rRNA sequences that have less than 97% identity are most likely derived from different bacterial species (Stackebrandt, E., and B. M. Goebel. 1994. A place for DNA—DNA reassociation and 16S ribosomal-RNA sequence analysis in the present species definition in bacteriology. *Int. J. Syst. Bacteriol.* 44: (4) 846–849). Since the 16S rDNA sequences derived from RA1, RA2, RA3, RA6, and RA9 have less than 96% identity with the most similar 16S sequences already present in GenBank, the 16S rDNA sequences from RA1, RA2, RA3, RA6, and RA9 are significantly different from any other 16S rDNA or 16S rRNA sequence previously known to the art.

TABLE 3

Comparison of 16S rDNA sequences from wastewater bacteria to GenBank sequences

| | | GenBank Sequence with Highest Identity | |
|---|---|---|---|
| Strain | Accession No. | Type of Bacteria | % Identity |
| RA1 | U51101 | Denitrifying Fe<II>-oxidizing bacteria | 94 |
| RA2 | U51101 | Denitrifying Fe<II>-oxidizing bacteria | 95 |
| RA3 | X77450 | *Corynebacterium aquaticum* | 95 |
| RA6 | D14320 | *Brachymonas denitrificans* | 92 |
| RA9 | D14320 | *Brachymonas denitrificans* | 92 |

Example 3

Unique 16S rRNA Sequences Derived from Novel Bacteria Isolated from a Wastewater Bioreactor Example 3 demonstrates that unique sequences can be derived from the 16S rDNA sequences of bacterial isolates EMB14A, NBYE13, RA1, RA2, RA3, RA6, and RA9. These sequences could be used to identify and/or detect these bacteria.

A computer program was written to analyze every contiguous 18 base pair fragment that could be produced from the 16S sequences for strains RA1, RA2, RA3, RA6, RA9, EMB14A and NBYE13. The program broke each 16S sequence into all possible 18 base pair fragments by sliding one base at a time along the sequence and selecting the next 17 bases. The program then compared each of these fragments to a 16S rDNA database created by the Ribosomal Database Project at Michigan State University. All the sequence fragments from a particular 16S sequence that did not produce an exact match using a pattern search program (Scan_for_Matches available from Ross Overbeek, MCS, Argonne National Laboratories, Argonne, Ill. 60439) were then placed into a separate file for each strain. Each strain file was imported into Sequencher (version 3. 1, Gene Codes Corporation), and the fragments were assembled into larger contigs. The resulting contigs were compared against the Genbank Nucleotide Database using the Blast algorithm (NCBI). The resulting alignments were examined and regions were identified that had high frequencies of unmatched bases. Specific regions in the 16S rDNA sequences for strains RA1, RA2, RA6, RA9, EMB14A, and NBYE13 were identified that were unique in that exact matches to the regions did not appear in any other sequence in GenBank.

No unique sequences were found for the RA3 16S rDNA. A Blast alignment of the RA3 16S rDNA sequence and the closest matching 16S rDNA sequence from GenBank revealed a region of about 58 bases that contained 9 mismatches. This region was compared against the Genbank database and was found to be identical to several 16S sequences. However, none of these sequences were represented among the 10 GenBank sequnses that were most similar to the full length RA3 16S rDNA sequence. The full RA3 16s rDNA, the 58 base pair sequence, the 5 GenBank sequences most similar to the full length sequence, and the 5 GenBank sequences most similar to the 58 base pair sequence were aligned using ClustalW. Based on the the multiple alignment, a set of primers was designed that could be used to amplify by PCR a 289 base pair sequence from only the RA3 16S rDNA sequence.

EMB14A

[SEQ ID NO:16]
5'-TCCCGGCCCCGAAAGGGAAACA-3'

[SEQ ID NO:17]
5'-CCTCAAAAAGAGCGTATCC-3'

NBYE13

[SEQ ID NO:18]
5'-GTAGCGCAAGGCCCTTGCGAGTCCCCTGCTTTCATCCACGGATCTC 3'

RA1

[SEQ ID NO:19]
5'-CCGCAAGGCCTCACGCGTTT-3'

[SEQ ID NO:20]
5'-ACGGAAAGGGCTCTCTCTAATACAGGGGGCAT-3'

[SEQ ID NO:21]
5'-TGAAGGCAATCCCGTGGGCA-3'

[SEQ ID NO:22]
5'-ACGGAATCCTGCAGAGACGCAGGAGTGCTCGA-3'

RA2

[SEQ ID NO:23]
5'-TCGAGCACTCCTGCGTCTCTGCAGGATTCCGT-3'

[SEQ ID NO:24]
5'-ATGCCCCCTGTATTAGAGAGAGCCC-3'

RA6

[SEQ ID NO:25]
5'-GCGAGCACTCCCACATCTCTGCG-3'

[SEQ ID NO:26]
5'-GTGCCCTCTTTATTAGAAAGAGCCC-3'

RA9

[SEQ ID NO:27]
5'-TCCGTGGATGAAAGCAGGGGACTCGCAAGG-3'

[SEQ ID NO:28]
5'-CTCGCAAGGGCCTTGCGCTAC-3'

RA3

[SEQ ID NO:29]
5'-CGCGCGAAGGCATCTTCTGCGCG-3'

[SEQ ID NO:30]
5'-TGCAGGTACCGTCACTTT-3'

Example 4

Physiological Characterization of Novel Bacteria from a Wastewater Bioreactor

Example 4 demonstrates that several strains of bacteria from a wastewater bioreactor were able to degrade organic and inorganic compounds that are likely to be found in a biological wastewater treatment system.

Acetate and pyruvate are frequently metabolic intermediates produced as the result of bacterial degradation of carbohydrates such as glucose (A. G. Moat and J. W. Foster. 1995. *Microbial Physiology*, 3rd edition. Wiley-Liss, New York) and aromatic compounds such as toluene and benzene (Assinder and Williams, *Adv. Microb. Physiol.* 31:2–69 (1990)). Strains RA1, RA2, RA3, RA6, RA9, EMB14A, and NBYE13 were tested for growth with these compounds supplied as the carbon source. A commercial preparation of acetate differential agar (BBL) was used to determine if the bacterial strains utilized acetate. Acetate utilization is indicated by a change from green to blue in the color of the agar culture medium. The culture medium was inoculated by streaking bacteria on the surface of the agar with an inoculating loop according to procedures well known to those skilled in the art. After 24 hours at 25° C., RA1 and RA2 were positive for acetate utilization whereas all of the other strains were negative. Strains RA2, RA3, RA6, RA9, EMB14A, and NBYE13 were tested for growth with pyruvate in Liquid R2A medium (0.5 g/l yeast extract, 0.5 g/l protease peptone No. 3, 0.5 g/l casamino acids, 0.3 g/l dibasic potassium phosphate, and 0.05 g/l magnesium sulfate) supplemented with 5 mM sodium pyruvate. Each strain was inoculated into 20 ml of liquid R2A medium in a 250 ml screw cap Erlenmyer flask and incubated in a reciprocal shaking water bath at 30° C. Growth was measured by withdrawing samples and measuring the optical density at 600 nm with a Pharmacia Biotech Ultrospec 3000 spectrophotometer. The cultures of all of the strains except RA2 increased at least five-fold, and hence, were positive for growth with pyruvate as carbon source.

Benzoate and/or catechol are frequently metabolic intermediates produced as the result of bacterial degradation of aromatic compounds such as toluene and benzene (Assinder and Williams, *Adv. Microb. Physiol*. 31:2–69 (1990)). Bacteria were inoculated into 20 ml of liquid R2A medium supplemented with 5 mM sodium benzoate or 5 mM catechol in a 250 ml screw cap Erlenmyer flask and incubated in a reciprocal shaking water bath at 30°C. Growth was measured by withdrawing samples and measuring the optical density at 600 nm with a Pharmacia BIOTECH ULTROSPEC™3000 spectraphotometer. Strains RA6, RA9 and NBYE13 increased at least 5-fold in 72 hours in medium with sodium benzoate, and hence, were positive for growth with benzoate as carbon source. Strain RA3 increased 8-fold in 48 hours in medium with catechol, and hence, was positive for growth with catechol as carbon source.

Nitrate is an organic ion that frequently must be removed from wastewater. Biological denitrification is commonly used to remove nitrate from wastewater, and many species of wastewater bacteria are known to reduce nitrate to any of several products including nitrite, $NO_2$, $N_2O$, and $N_2$ (Bitton, G. 1994. supra). Bacteria were inoculated into 22 ml of liquid R2A medium supplemented with 10 mM $KNO_3$ and 5 mM glucose in 25 ml serum vials. Triplicate cultures were established for each strain that was tested. The cultures were incubated at 30° C. Samples were removed from each vial with a syringe and tested for nitrate and nitrite using commercial test strips (EM Science, Gibbstown, N.J.). After one week of incubation, the RA6 cultures each contained approximately 1 g/l of nitrite, and the EMB14A cultures contained approximately 0.3 g/l of nitrite. After an additional week, the RA6 cultures each contained approximately 2 g/l of nitrite, and the EMB14A cultures contained approximately 1 g/l of nitrite. The level of nitrate remained constant and no nitrite was detected in cultures of the other strains that were tested. Similarly, the level of nitrate remained constant and no nitrite was detected in uninoculated control cultures. Hence, strains RA6 and EMB14A were able to reduce nitrate to nitrite.

What is claimed is:

1. An isolated 16S rDNA molecule indicative of the presence of an activated sludge bacterial strain selected from the group consisting of:
   (a) the nucleic acid molecule of SEQ ID NO:5; and
   (b) the isolated nucleic acid molecule that is completely complementary to (a).

2. An isolated 16S rDNA molecule indicative of the presence of an activated sludge bacterial strain selected from the group consisting of:
   (a) the nucleic acid molecule consisting of SEQ ID NO:29;
   (b) the nucleic acid molecule consisting of SEQ ID NO:30; and
   (c) the isolated nucleic acid molecule that is completely complementary to (a) or (b).

* * * * *

SEQUENCE LISTING

```
<160> NUMBER OF SEQ ID NOS: 30

<210> SEQ ID NO 1
<211> LENGTH: 1385
<212> TYPE: DNA
<213> ORGANISM: Unknown Organism
<220> FEATURE:
<223> OTHER INFORMATION: Description of Unknown Organism:  Paracoccus sp
<220> FEATURE:
<223> OTHER INFORMATION: Nucleotide sequence of 16S rDNA corresponding
      to strain EMB 14A

<400> SEQUENCE: 1
ccccagtcgc tgagcctacc gtggtccgct gcctcccgta agggttagcg cacggccgtc      60
gggtagaccc aactcccatg gtgtgacggg cggtgtgtac aaggcccggg aacgtattca     120
ccgcggcatg ctgttccgcg attactagcg attccaactt catgggtcg agttgcagac     180 cccaatccga actgagacgg cttttggga ttaacccatt gtcaccgcca ttgtagcacg     240
tgtgtagccc aacccgtaag ggccatgagg acttgacgtc atccacacct tcctccgact     300
tatcatcggc agttcttcca gagtgcccaa ccgaatgatg gcaactggaa gtgtgggttg     360
cgctcgttgc cggacttaac cgaacatctc acgacacgag ctgacgacag ccatgcagca     420
cctgtctccc ggccccgaaa ggggaaacac catctctggt gcggtccgag gatgtcaagg     480
gttggtaagg ttctgcgcgt tgcttcgaat taaaccacat gctccaccgc ttgtgcgggc     540
ccccgtcaat tcctttgagt tttaatcttg cgaccgtact ccccaggcgg aatgcttaat     600
ccgttaggtg tgtcaccgaa cagcatgctg cccgacgact ggcattcatc gtttacgcg      660 tggactacca gggtatctaa tcctgtttgc tccccacgct ttcgcacctc agcgtcagta     720
tcgagccagt gagccgcctt cgccactggt gttcctccga atatctacga atttcacctc     780
tacactcgga attccactca cctctctcga actccagact gacagttttg aaggcagttc     840
cggggttgag ccccgggatt tcaccccaa ctttccagtc cgcctacgtg cgctttacgc      900
ccagtaattc cgaacaacgc tagccccctc cgtattaccg cggctgctgg cacggagtta     960
gccgggcgtt cttctgctgg taccgtcatt atcttccag ctgaaagagc tttacaaccc    1020
taaggccttc atcactcacg cggcatggct agatcagggt tgccccatt gtctaagatt    1080
```

-continued

```
ccccactgct gcctcccgta ggagtctggg ccgtgtctca gtcccagtgt ggctgatcat      1140
cctctcaaac cagctatgga tcgtcggctt ggtaggccat taccccacca actacctaat      1200
ccaacgcggg ccgatccttc gccgataaat ctttcctcaa aaagagcgta tccggtatta      1260
ctcccagttt cccagggcta ttccgaagca aagggcacgt tcccacgcgt tactcacccg      1320
tccgccgcta ggaccgaagt cctcgctcga cttgcatgtg ttaggcctgc cgccagcgtt      1380
cgttc                                                                  1385

<210> SEQ ID NO 2
<211> LENGTH: 1467
<212> TYPE: DNA
<213> ORGANISM: Unknown Organism
<220> FEATURE:
<223> OTHER INFORMATION: Description of Unknown Organism:  Brachymonas
<220> FEATURE:
<223> OTHER INFORMATION: Nucleotide sequence of 16S rDNA corresponding
      to strain NBYE13

<400> SEQUENCE: 2
gttacgactt cacccccagtc acgaacccca ccgtggcaag cgccctcctt gcggttaggc      60
tacctgcttg tggtgagacc cgctcccatg gtgtgacggg cggtgtgtac aagacccggg     120
aacgtattca ccgtgacatg ctgatccacg attactagca attccgactt cacgcagtcg     180
agttgcagac tgcgatccgg actacgaccg gctttatggg attggcttca cctcgcggct     240
tcgctgccct ttgtaccggc cattgtatga cgtgtgtagc cccacctata agggccatga     300
ggacttgacg tcatccccac cttcctccgg tttgtcaccg gcagtcccat cagagtgccc     360
tttcgtagca actgatggca agggttgcgc tcgttgcggg acttaaccca acatctcacg     420
acacgagctg acgacagcca tgcagcacct gtgttatggc tctcttgcga gcactcccac     480
atctctgcgg gattccatac atgtcaaagg tgggtaaggt ttttcgcgtt gcatcgaatt     540
aaaccacatc atccaccgct tgtgcgggtc ccgtcaatt cctttgagtt ttaaccttgc     600
ggccgtactc cccaggcggt caacttcacg cgttagcttc gttactgaag aaataaatcc     660
ccaacaacca gttgacatcg tttagggcgt ggactaccag ggtatctaat cctgtttgct     720
ccccacgctt tcgtgcatga gcgtcagtac aggcccaggg gactgccttc gccatcggtg     780
ttcctccgca tatctacgca tttcactgct acacgcggaa ttccatcccc ctctgccgta     840
ctccagcctt gcagtcacaa tggcagttcc caggttgagc ccggggattt caccactgtc     900
ttgcaagacc gcctgcgcac gctttacgcc cagtaattcc gattaacgct cgcaccctac     960
gtattaccgc ggctgctggc acgtagttag ccggtgctta ttcttacggt accgtcatgt     1020
gccctcttta ttagaaagag ccctttcgtt ccgtacaaaa gcagtttaca cccgaaggc     1080 cttcatcctg cacgcggcat ggctggatca ggcttgcgcc cattgtccaa aattccccac     1140
tgctgcctcc cgtaggagtt cgggccgtgt ctcagtcccg atgtggctga tcatcctctc     1200
agaccagcta cagatcgcag gcttggtggg cctttacccc accaactacc taatctgaca     1260
tcggccgctc cagtagcgca aggcccttgc gagtcccctg ctttcatcca cggatctcat     1320
gcggtattaa tccggctttc gccgagctat ccgcactac cgggcacgtt ccgatgcttt     1380
actcacccgt tcgccactcg ccgccatccc gaaggacgcg ctgccgttcg acttgcatgt     1440
gtaaggcatg ccgccagcgt tcaatct                                         1467
```

```
<210> SEQ ID NO 3
<211> LENGTH: 1450
<212> TYPE: DNA
<213> ORGANISM: Unknown Organism
<220> FEATURE:
<223> OTHER INFORMATION: Description of Unknown Organism:
      Denitrifying bacteria
<220> FEATURE:
<223> OTHER INFORMATION: Nucleotide sequence of 16S rDNA corresponding
      to strain RA1

<400> SEQUENCE: 3
agattgaacg ctggcggaat gctttacaca tgcaagtcga gcggcagcgc ggggcaacct    60
ggcggcgagc ggcgaacggg tgagtaacac atcggaacgt gcccagacgt ggggatagc   120 ccggcgaaag ccggattaat accgcatgtg atctgaggat gaaagtgggg gaccgcaagg   180
cctcacgcgt ttggagcggc cgatggcaga ttaggtagtt ggtggggtaa aggcttacca   240
agcctgcgat ctgtagctgg tctgagagga tgatcagcca cactgggact gagacacggc   300
ccagactcct acgggaggca gcagtgggga attttggaca atgggcgcaa gcctgatcca   360
gccattccgc gtgcaggacg aaggcttcgg gttgtaaact gcttttgtac ggaacgaaa   420 gggctctctc taatacaggg ggcatatgac ggtaccgtaa gaataagcac cggctaacta   480
cgtgccagca gccgcggtaa tacgtagggt gcaagcgtta atcggaatta ctgggcgtaa   540
agcgtgcgca ggcggttttg taagacagag gtgaaatccc cgggctcaac ctgggaactg   600
cctttgtgac tgcaaggctg gagtgcggca gaggggatg gaattccgcg tgtagcagtg   660
aaatgcgtag atatgcggag gaacaccgat ggtgaaggca atcccgtggg catgcactga   720
cgctcatgca cgaaagcgtg gggagcaaac aggattagat accctggtag tccacgccct   780
aaaacgatgt caactggttg ttgggaattc attttctcag taacgaagct aacgcgtgaa   840
gttgaccgcc tggggagtac ggccgcaagg ttaaaactca aaggaattga cggggacccg   900
cacaagcggt ggatgatgtg gtttaattcg atgcaacgcg aaaaacctta cccacctttg   960
acatgtacgg aatcctgcag agacgcagga gtgctcgaaa gagagccgta acacaggtgc  1020
tgcatggctg tcgtcagctc gtgtcgtgag atgttgggtt aagtcccgca acgagcgcaa  1080
cccttgccat tagttgctac gaaagggcac tctaatggga ctgccggtga caaaccggag  1140
gaaggtgggg atgacgtcaa gtcctcatgg cccttatagg tggggctaca cacgtcatac  1200
aatggctggt acaaagggtt gccaacccgc gaggggagc caatcccaca agccagtcg   1260 tagtccggat cgcagtctgc aactcgactc cgtgaagtcg gaatcgctag taatcgtgga  1320
tcagcatgtc acggtgaata cgttccccgg gtcttgtaac accgcccgt tcaacaccat  1380 ggagcggttc tgccagaagt agttagccta accgcaagga gggcgattac cacggcaggt  1440
tcgtgatggg                                                        1450

<210> SEQ ID NO 4
<211> LENGTH: 1453
<212> TYPE: DNA
<213> ORGANISM: Unknown Organism
<220> FEATURE:
<223> OTHER INFORMATION: Description of Unknown Organism:
      Dinitrifying bacteria
<220> FEATURE:
<223> OTHER INFORMATION: Nucleotide sequence of rDNA corresponding to
      strain RA2

<400> SEQUENCE: 4
ccccagtcac gaaccctgcc gtggtaatcg ccctccttgc ggttaggcta actacttctg    60
```

```
gcagaacccg ctcccatggt gtgacgggcg gtgtgtacaa gacccgggaa cgtattcacc      120
gtgacatgct gatccacgat tactagcgat tccgacttca cgcagtcgag ttgcagactg      180
cgatccggac tacgactggc tttgtgggat tggctccccc tcgcgggttg gcaaccettt      240 gtaccagcca ttgtatgacg tgtgtagccc cacctataag ggccatgagg acttgacgtc      300
atccccacct tcctccggtt tgtcaccggc agtcccatta gagtgcccett tcgtagcaac      360 taatggcaag ggttgcgctc gttgcgggac ttaacccaac atctcacgac acgagctgac      420
gacagccatg cagcacctgt gttacggctc tctttcgagc actcctgcgt ctctgcagga      480
ttccgtacat gtcaaaagtg ggtaaggttt tcgcgttgc atcgaattaa accacatcat       540
ccaccgcttg tgcgggtccc cgtcaattcc tttgagtttt aaccttgcgg ccgtactccc      600
caggcggtca acttcacgcg ttagcttcgt tactgagaaa atgaattccc aacaaccagt      660
tgacatcgtt tagggcgtgg actaccaggg tatctaatcc tgtttgctcc ccacgctttc      720
gtgcatgagc gtcagtgcag gcccagggga ttgccttcgc catcggtgtt cctccgcata      780
tctacgcatt tcactgctac acgcggaatt ccatcccct ctgccgcact ccagccttgc       840
agtcacaaag gcagttccca ggttgagccc ggggatttca cctctgtctt acaaaaccgc      900
ctgcgcacgc tttacgccca gtaattccga ttaacgcttg cacccctacgt attaccgcgg      960 ctgctggcac gtagttagcc ggtgcttatt cttacggtac cgtcatatgc cccctgtatt     1020
agagagagcc ctttcgttcc gtacaaaagc agtttacaac ccgaaggcct tcgtcctgca     1080
cgcggaatgg ctggatcagg cttgcgccca ttgtccaaaa ttccccactg ctgcctcccg     1140
taggagtctg ggccgtgtct cagtcccagt gtggctgatc atcctctcag accagctaca     1200
gatcgcaggc ttggtaagcc tttacccac caactaccta atctgccatc ggccgctcca      1260
aacgcgtgag gccttgcggt cccccacttt catcctcaga tcacatgcgg tattaatccg     1320
gctttcgccg ggctatcccc cacgtctggg cacgttccga tgtgttactc acccgttcgc     1380
cgctcgccgc caggttgccc cgcgctgccg ctcgacttgc atgtgtaaag cattccgcca     1440
gcgttcaatc tga                                                        1453
```

<210> SEQ ID NO 5
<211> LENGTH: 1449
<212> TYPE: DNA
<213> ORGANISM: Unknown Organism
<220> FEATURE:
<223> OTHER INFORMATION: Description of Unknown Organism:
   Corynebacterium Microbacterium
<220> FEATURE:
<223> OTHER INFORMATION: Nucleotide sequence of 16S rDNA corresponding
   to strain RA3

<400> SEQUENCE: 5

```
cttagtctta atcaccgatc ccaccttcga cagctccctc cttgcggttg ggccactggc       60
ttcgggtgtt accgactttc atgacttgac gggcggtgtg tacaaggccc gggacgtatt      120
caccgcagcg ttgctgatct gcgattacta gcgactccga cttcatgagg tcgagttgca      180
gacctcaatc cgaactgaga ccgactttt gggattcgct ccaccttacg gtattgcagc      240
cctttgtatc ggccattgta gcatgcgtga agcccaagac ataaggggca tgatgatttg      300
acgtcatccc caccttcctc cgagttgacc ccggcagtct cctatgagtt cccaccatga     360
cgtgctggca acatagaacg agggttgcgc tcgttgcggg acttaaccca acatctcacg     420
acacgagctg acgacaacca tgcaccacct gtttacgagt gtccaaagag ttgaccattt     480
```

```
ctggcccgtt ctcgtatatg tcaagccttg gtaaggttct tcgcgttgca tcgaattaat      540
ccgcatgctc cgccgcttgt gcgggccccc gtcaattcct ttgagtttta gccttgcggc      600
cgtactcccc aggcgtggaa cttaatgcgt tagctgcgac acagaaaccg tggaatggcc      660
cctacatcta gttcccaacg tttacggcgt ggactaccag ggtatctaat cctgttcgct      720
ccccacgctt tcgctcctca gcgtcagtta cggcccagag atctgccttc gccatcggtg      780
ttcctcctga tatctgcgca ttccaccgct acaccaggaa ttccaatctc ccctaccgca      840
ctctagtctg cccgtaccca ctgcaggctg gaggttgagc ctccagtttt cacagcagac      900
gcgacaaacc gcctacgagc tctttacgcc caataattcc ggataacgct tgcaccctac      960
gtattaccgc ggctgctggc acgtagttag ccggtgcttt ttctgcaggt accgtcactt     1020
tcgcttcttc cctactaaaa gaggtttaca acccgaaggc cgtcgtccct cacgcggcgt     1080
tgctgcatca ggcttgcgcc cattgtgcaa tattccccac tgctgcctcc cgtaggagtc     1140
tgggccgtgt ctcagtccca gtgtggccgg tcaccctctc aggccggcta cccgtcgtcg     1200
ccttggtggg ccgttacctc accaactagc tgataggccg cgagtccatc cttgaccgaa     1260
attctttcca cgcgcagaag atgccttcgc gcgtcgtatc cggtattaga cgtcgtttcc     1320
aacgcttatc ccagagtcaa gggcaggtta ctcacgtgtt actcacccgt tcgccactaa     1380
tccaccagag caagctccgg cttcatcgtt cgacttgcat gtgttaagca cgccgccagc     1440
gttcatcct                                                             1449
```

<210> SEQ ID NO 6
<211> LENGTH: 1539
<212> TYPE: DNA
<213> ORGANISM: Unknown Organism
<220> FEATURE:
<223> OTHER INFORMATION: Description of Unknown Organism: Brachymonas
<220> FEATURE:
<223> OTHER INFORMATION: Nucleotide sequence of 16S rDNA corresponding
    to strain RA6

<400> SEQUENCE: 6

```
taaagcgtgc gcaggcggtc ttgcaagaca gtggtgaaat ccccgggctc aacctgggaa       60
ctgccattta cccttgttac gacttcaccc cagtcacgaa ccccaccgtg gcaagcgccc      120
tccttgcggt taggctacct gcttctggtg agacccgctc ccatggtgtg acgggcggtg      180
tgtacaagac ccgggaacgt attcaccgtg acatgctgat ccacgattac tagcgattcc      240
gacttcacgc agtcgagttg cagactgcga tccggactac gaccggcttt atgggattgg      300
cttcacctcg cggcttcgct gcccctttgta ccggccattg tatgacgtgt gtagccccac      360
ctataagggc catgaggact tgacgtcatc cccaccttcc tccggtttgt caccggcagt      420
cccatcagag tgccctttcg tagcaactga tggcaagggt tgcgctcgtt gcgggactta      480
acccaacatc tcacgacacg agctgacgac agccatgcag cacctgtgtt atggctctct      540
tgcgagcact cccacatctc tgcgggattc catacatgtc aaaggtgggt aaggtttttc      600
gcgttgcatc gaattaaacc acatcatcca ccgcttgtgc gggtcccgt caattccttt       660 gagttttaac cttgcggccg tactccccag gcggtcaact tcacgcgtta gcttcgttac      720
tgaagaaata aatccccaac aaccagttga catcgtttag ggcgtggact accagggtat      780
ctaatcctgt ttgctcccca cgctttcgtg catgagcgtc agtacaggcc caggggactg      840
ccttcgccat cggtgttcct ccgcatatct acgcatttca ctgctacacg cggaattcca      900
tccccctctg ccgtactcca gccttgcagt cacaatggca gttcccaggt tgagcccggg      960
```

-continued

```
gatttcacca ctgtcttgca agaccgcctg cgcacgcttt acgcccagta attccgatta    1020
acgctcgcac cctacgtatt accgcggctg ctggcacgta gttagccggt gcttattctt    1080
acggtaccgt catgtgccct ctttattaga aagagccctt tcgttccgta caaaagcagt    1140
ttacaacccg aaggccttca tcctgcacgc ggcatggctg gatcaggctt gcgcccattg    1200
tccaaaattc cccactgctg cctcccgtag gagttcgggc cgtgtctcag tcccgatgtg    1260
gctgatcatc ctctcagacc agctacagat cgcaggcttg gtgggccttt accccaccaa    1320
ctacctaatc tgacatcggc cgctccagta gcgcaaggcc cttgcgggtc ccctgctttc    1380
atccacggat ctcatgcggt attaatccgg cttcgccga gctatcccgc actaccgggc    1440
acgttccgat gctttactca cccgttcgcc actcgccgcc atcccgaagg acgcgctgcc    1500
gttcgacttg catgtgtaag gcatgccgcc agcgttcat                          1539
```

<210> SEQ ID NO 7
<211> LENGTH: 1454
<212> TYPE: DNA
<213> ORGANISM: Unknown Organism
<220> FEATURE:
<223> OTHER INFORMATION: Description of Unknown Organism: Brachymonas
<220> FEATURE:
<223> OTHER INFORMATION: Nucleotide sequence of the 16S rDNA
      corresponding to strain RA9

<400> SEQUENCE: 7

```
ttgaacgctg gcggcatgcc ttacacatgc aagtcgaacg gcagcgcgtc cttcgggatg      60
gcggcgagtg gcgaacgggt gagtaaagca tcggaacgtg cccggtagtg cgggatagct     120
cggcgaaagc cggattaata ccgcatgaga tccgtggatg aaagcagggg actcgcaagg    180
gccttgcgct actggagcgg ccgatgtcag attaggtagt tggtggggta aaggcccacc    240
aagcctgcga tctgtagctg gtctgagagg atgatcagcc acatcgggac tgagacacgg    300
cccgaactcc tacgggaggc agcagtgggg aattttggac aatgggcgca agcctgatcc    360
agccatgccg cgtgcaggat gaaggccttc gggttgtaaa ctgcttttgt acggaacgaa    420
agggctcttt ctaataaaga gggcacatga cggtaccgta agaataagca ccggctaact    480
acgtgccagc agccgcggta atacgtaggg tgcgagcgtt aatcggaatt actgggcgta    540
aagcgtgcgc aggcggtctt gcaagacagt ggtgaaatcc ccgggctcaa cctgggaact    600
gccattgtga ctgcaaggct ggagtacggc agagggggat ggaattccgc gtgtagcagt    660
gaaatgcgta gatatgcgga ggaacaccga tggcgaaggc agtcccctgg gcctgtactg    720
acgctcatgc acgaaagcgt ggggagcaaa caggattaga taccctggta gtccacgccc    780
taaacgatgt caactggttg ttggggattt atttcttcag taacgaagct aacgcgtgaa    840
gttgaccgcc tggggagtac ggccgcaagg ttaaaactca aaggaattga cggggacccg    900
cacaagcggt ggatgatgtg gtttaattcg atgcaacgcg aaaaacctta cccacctttg    960
acatgtatgg aatcccgcag agatgtggga gtgctcgcaa gagagccata acacaggtgc    1020
tgcatggctg tcgtcagctc gtgtcgtgag atgttgggtt aagtcccgca acgagcgcaa    1080
cccttgccat cagttgctac gaaagggcac tctgatggga ctgccggtga caaaccggag    1140
gaaggtgggg atgacgtcaa gtcctcatgg cccttatagg tggggctaca cacgtcatac    1200
aatggccggt acaaagggca gcgaagccgc gaggtgaagc caatcccata agccggtcg     1260 tagtccggat cgcagtctgc aactcgactg cgtgaagtcg gaatcgctag taatcgtgga    1320
```

```
tcagcatgtc acggtgaata cgttcccggg tcttgtacac accgcccgtc acaccatggg    1380
agcgggtctc accagaagca ggtagcctaa ccgcaaggag ggcgcttgcc acggtggggt    1440
tcgtgactgg ggtg                                                     1454
```

```
<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:  Primer
      used in the amplification of 16S rDNA

<400> SEQUENCE: 8
gagtttgatc ctggctcag                                                  19

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence:  Primer
      used in the amplification of 16S rDNA

<400> SEQUENCE: 9
taccttgtta cgactt                                                     16

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:  Primer
      used in the amplification of 16S rDNA
<220> FEATURE:
<223> OTHER INFORMATION: Y=C or T, M=A or C

<400> SEQUENCE: 10
gtgccagcag ymgcggt                                                    17

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:  Primer
      used in the amplification of 16S rDNA

<400> SEQUENCE: 11
gtgctccccc gccaattcct                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:  Primer
      used in the amplification of 16S rDNA

<400> SEQUENCE: 12
aggaattggc gggggagcac                                                 20

<210> SEQ ID NO 13
<211> LENGTH: 23
<212> TYPE: DNA
<213> ORGANISM: Artificial Sequence
```

-continued

```
<220> FEATURE:
<223> OTHER INFORMATION: Description of Artificial Sequence:  Primer
      used in the amplification of 16S rDNA

<400> SEQUENCE: 13
cacgagctga cgacgacagc cat                                            23

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:  Primer
      used in the amplification of 16S rDNA

<400> SEQUENCE: 14
atggctgtcg tcagctcgtg                                                20

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence:  Primer
      used in the amplification of 16S rDNA
<220> FEATURE:
<223> OTHER INFORMATION: K=G or T, R=A or G

<400> SEQUENCE: 15
accgckrctg ctggcac                                                   17

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:  Nucleotide
      sequence corresponding to a region on the 16S rDNA which is
      diagnostic for the strain EMB 14a

<400> SEQUENCE: 16
tcccggcccc gaaagggaa aca                                             23

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:
      Nucleotide sequence corresponding to a region on the 16S rDNA
      which is diagnostic for the strain EMB 14a

<400> SEQUENCE: 17
cctcaaaaag agcgtatcc                                                 19

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence:  Nucleotide
      sequence corresponding to a region on the 16S rDNA which is
      diagnostic for the strain NBYE13

<400> SEQUENCE: 18
gtagcgcaag gcccttgcga gtccctgct ttcatccacg gatctc                    46
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Nucleotide
      sequence corresponding to a region on the 16S rDNA which is
      diagnostic for the strain RA1

<400> SEQUENCE: 19
ccgcaaggcc tcacgcgttt                                                    20

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Nucleotide
      sequence corresponding to a region on the 16S rDNA which is
      diagnostic for the strain RA1

<400> SEQUENCE: 20
acggaaaggg ctctctctaa tacaggggc at                                       32

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Nucleotide
      sequence corresponding to a region on the 16S rDNA which is
      diagnostic for the strain RA1

<400> SEQUENCE: 21
tgaaggcaat cccgtgggca                                                    20

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Nucleotide
      sequence corresponding to a region on the 16S rDNA which
      diagnostic for the strain RA1

<400> SEQUENCE: 22
acggaatcct gcagagacgc aggagtgctc ga                                      32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Nucleotide
      sequence corresponding to a region on the 16S rDNA which is
      diagnostic for the strain RA2

<400> SEQUENCE: 23
tcgagcactc ctgcgtctct gcaggattcc gt                                      32

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Nucleotide
      sequence corresponding to a region on the 16s rDNA which is
      diagnostic for the strain RA2
```

```
<400> SEQUENCE: 24 atgcccctg tattagagag agccc                                         25

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Nucleotide
      sequence corresponding to a region on the 16S rDNA which is
      diagnostic for the strain RA6

<400> SEQUENCE: 25
gcgagcactc ccacatctct gcg                                          23

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Nucleic
      acid sequence corresponding to a region on the 16s rDNA which is
      diagnostic for the strain RA6

<400> SEQUENCE: 26
gtgccctctt tattagaaag agccc                                        25

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Nucleotide
      sequence corresponding to a region on the 16S rDNA which is
      diagnostic for the strain RA9

<400> SEQUENCE: 27
tccgtggatg aaagcagggg actcgcaagg                                   30

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Nucleotide
      sequence corresponding to a region on the 16S rDNA which is
      diagnostic for the strain RA9

<400> SEQUENCE: 28
ctcgcaaggg ccttgcgcta c                                            21

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Nucleotide
      sequence corresponding to a region on the 16S rDNA which is
      diagnostic for the strain RA3

<400> SEQUENCE: 29
cgcgcgaagg catcttctgc gcg                                          23

<210> SEQ ID NO 30
<211> LENGTH: 18
<212> TYPE: DNA
<213> ORGANISM: Artificial Sequence
```

```
<220> FEATURE:
<223> OTHER INFORMATION: Description of Artificial Sequence:  Nucleotide
      sequence corresponding to a region on the 16S rDNA which is
      diagnostic for the strain RA3

<400> SEQUENCE: 30
tgcaggtacc gtcactttt                                                       18
```